United States Patent [19]

Galbraith

[11] 4,361,551

[45] Nov. 30, 1982

[54] METHOD OF ENZYMATIC DEBRIDEMENT

[75] Inventor: William Galbraith, Newark, Del.

[73] Assignee: Riker Laboratories, Inc., Northridge, Calif.

[21] Appl. No.: 260,711

[22] Filed: May 5, 1981

Related U.S. Application Data

[63] Continuation of Ser. No. 91,040, Nov. 5, 1979, abandoned.

[51] Int. Cl.$^3$ ............................................. A61K 37/48
[52] U.S. Cl. ..................................................... 424/94
[58] Field of Search .......................................... 424/94

[56] References Cited

U.S. PATENT DOCUMENTS 4,197,291  4/1980  Klein et al. ............................ 424/94

OTHER PUBLICATIONS

Silverstein et al., Surgery, 73 (1) pp. 15–22 (Jan. 1973).
Levine et al., Plastic and Reconstr. Surgery, 52 (4) pp. 413–424 (Oct. 1973).
Levinson et al., Ann. Surg., 180 (4) pp. 670–704 (1974).

*Primary Examiner*—Sam Rosen
*Attorney, Agent, or Firm*—Cruzan Alexander; Donald M. Sell; Carolyn A. Bates

[57] ABSTRACT

A method of treating devitalized tissue in mammals is disclosed. The method comprises applying to the devitalized tissue a composition comprising an enzyme mixture derived from crude bromelain which exhibits 15 to 35 units of protease activity per milligram of protein in the presence of cysteine and from 0.5 to 5 units of collagenase activity per milligram of protein and an inert solvent carrier containing at least 60 percent water.

2 Claims, No Drawings

METHOD OF ENZYMATIC DEBRIDEMENT

This is a continuation of application Ser. No. 91,040, filed Nov. 5, 1979, now abandoned.

This invention relates to a method of treating devitalized tissue such as burn eschar to effect its removal from surrounding healthy tissue. More specifically, the invention relates to a method of removing devitalized tissue using an enzyme mixture derived from crude, commercially-available bromelain.

The presence of devitalized or dead tissue in the skin of a human or animal patient poses a serious health hazard to the patient. If the surface area involved is extensive, as in the case of a patient with third degree burns over a large portion of the body, a life threatening situation exists. The devitalized tissue provides an ideal culture medium for bacteria, and systemic infection is the primary cause of death in severely burned patients. In addition to infection, the presence of devitalized tissue, if extensive enough, may interfere with the normal homeostatic processes of the body such as temperature control and electrolyte balance.

Accordingly, to prevent proliferation of bacteria and to minimize insult to normal bodily functions, it is generally agreed that devitalized tissue should be removed as soon as possible to speed wound closure by normal healing processes or skin grafting.

The primary method of removing devitalized tissue practiced today is surgery. Surgical debridement, however, has a number of attendant disadvantages including substantial blood loss, sacrifice of some healthy tissue, and the inherent risks associated with anesthesia.

As an alternative to surgical debridement, considerable effort has been made to discover a topical agent which will remove devitalized tissue from healthy tissue by chemical means. Of the agents tried, among the most successful experimentally have been certain plant and bacterial proteolytic enzymes. There have been some bacterial collagenase preparations which have worked effectively in certain laboratory animals, but these have not been uniformly effective when applied to human burns. "Travase" a commercial preparation of proteolytic enzyme(s) prepared from *B. Subtilis* has been used with some success on human patients. A summary of chemical agents evaluated for wound debriding activity is found in an article by Levenson et al, "Chemical Debridement of Burns" *Ann. Surg.* 180 No. 4, pp. 670–704(1974).

The aforementioned Levenson article deals at some length with studies on bromelain, a crude mixture of colloids precipitated from the juice of pineapple stems, as a debriding agent. Bromelain is known to exhibit considerable enzyme activity including proteolytic activity. This fact coupled with its commercial availability has made bromelain a likely candidate for study as a debriding agent. Other investigators who have reported debriding studies with bromelain include: Levine et al, "Debridement of Experimental Skin Burns of Pigs with Bromelain, a Pineapple-Stem Enzyme" *Plastic and Reconstruction Surgery*, Vol. 52, No. 4, pp. 413-424 (1973) and Silverstein et al, "In Vitro Evaluation of Enzymatic Debridement of Burn Wound Eschar" *Surgery*, Vol. 73, No. 1, pp. 15-22 (1973).

Generally most of the reported studies on bromelain as a debriding agent were done using commercially available stem bromelain in a conventional vehicle.

Commercially-available bromelain is a crude mixture of many colloids (including protein, carbohydrates, and mucopolysaccharides) inorganic salts and simpler organic materials which are precipitated from the juice of the pineapple stem by acetone. Protein generally constitutes about 50% of the total weight of the dried precipitate, inorganic materials, principally cations (calcium, magnesium potassium, copper and iron) generally made up to 10-15% of the total weight. The balance is assumed to be complex carbohydrate materials of the nature of polyuronides and glycosides.

The debriding activity of crude bromelain has generally proven to be inconsistent and non-reproducible. Accordingly, several attempts have been made heretofore to isolate the active debriding agent from crude bromelain. For example, Levenson et al, supra, fractionated commercial bromelain using various physicochemical techniques in an attempt to isolate and characterize the fraction or fractions active in wound debridement. According to their isolation technique, bromelain was partially solubilized in tris-buffer, pH 7.4 and placed on Sephadex G-100 columns and eluted with tris-buffer, pH 7.4, or alternatively, DEAE ion exchange columns were used and elution was with 0.02 M and 0.5 M sodium citrate, pH 6.0. In each case, the proteolytic activity of the various fractions against casein, the ability to attack burn eschar in vitro and in vivo and nitrogen content correlated closely. Amylase activity was also present in these fractions indicating more than one enzyme was likely present in each of the collected fractions showing debriding activity. Other than these general observations, no concrete information regarding the active debriding component of crude bromelain is provided by these investigators.

A more refined attempt to isolate the active debriding agent from commercial stem bromelian was carried out by Klein and Houck. In pending U.S. application Ser. No. 887,607 filed Mar. 17, 1978, (South African Pat. No. 77/0209) Klein and Houck describe a process for isolating what they believe to be the active debriding agent of stem bromelain. The product obtained by Klein and Houck is characterized as water-soluble, heat-labile, free of caseinolytic activity, having a peak isoelectric point at 6, a peak in the ultraviolet region of the spectrum at 280 nm, and comprising at least two subunits, each with a molecular weight of from 14,300 to 15,000 daltons.

The present invention differs from prior art methods of debriding by using a mixture of enzymes derived from crude bromelain having enzyme activity and other characterizing features different from prior art bromelain products used for this purpose. The enzyme mixture is obtained by a unique process which is the subject of co-pending U.S. patent application Ser. No. 91,041 filed on even date herewith, and exhibits consistently high and reproducible activity in the debridement of devitalized tissue in mammals.

According to the present invention, there is provided a method of treating devitalized tissue comprising applying to the tissue a composition comprising an effective amount of an enzyme mixture derived from crude bromelain which exhibits about 15 to 35 units of protease activity per milligram of protein when activated with cysteine, 0.3 to 5 units of protease activity per milligram of protein without cysteine and 0.5 to 5 units of collegenase activity per milligram of protein and an inert solvent carrier containing at least sixty percent water. In addition to protease and collagenase activity the enzyme mixture preferably exhibits catechol oxidase activity of 0.1 to 3 units per milligram of protein.

The enzyme composition digests the devitalized tissue and loosens it from the surrounding healthy tissue so that it can be easily removed by wiping. The composition is allowed to remain in contact with the devitalized tissue for a sufficient period of time to loosen the devitalized tissue, generally about 2 to 4 hours, during which time it is preferably covered with an occlusive wrap and kept warm (about 37° C.).

For purposes of the invention, the protease activity of the enzyme mixture is determined using the azoalbumin protease assay (Tomarelli, J. Lab. Clin. Med. 34, 428 (1949). According to the assay a test sample is prepared with the following materials:

Buffer: 0.1 M Tris.$PO_4$ pH 7.4
(0.1 M trishydroxymethylaminomethane base titrated to pH with $H_3PO_4$)

Substrate: 5 mg/ml Azoalbumin (Sigma Biochemicals, St. Louis, Mo.) in buffer, 0.25 ml/tube Optional addition: 0.05 M cysteine in buffer, 0.1 m/tube Enzyme Mixture: 0.1 ml of 1 mg/ml (in saline, $H_2O$ or buffer) without cysteine or 0.02 ml of 1 mg/ml (in saline, water or buffer) with cysteine Total Volume: 1 ml, brought to volume with $H_2O$ The enzyme, water and cysteine (optional) are first mixed together and warmed to 37° C. The substrate is then added at timed intervals of 15 seconds. After incubation for 15 minutes at 37° C., the reaction is stopped by the addition of 1 ml of 10% trichloroacetic acid. The tube is allowed to stand for 10 minutes and then centrifuged at 2000–5000 x g for 20 minutes. The absorbance of the supernatant versus water at 370 nm is read on a UV/Visible spectrophotometer. A substrate and sample blank must be included. One unit of activity in this assay is equivalent to the hydrolysis of 1 mg of azoalbumin in 15 minutes at pH 7.4° and 37° C. Generally, the average of two to four tubes are taken for each sample.

When no cysteine is included, active enzyme mixtures generally have protease activity of 0.6 to 3.0 units per mg of protein, although the range may extend from 0.3 to 5.0 units. Preferably activity is at last 1.5 units. When cysteine is included, the units are generally 20 to 30 units per mg of protein, although the range may extend from 15 to 35 units. Preferably activity is at least 20 units. The ratio of protease activity with cysteine to unactivated protease activity is preferably between 10 and 15. This is in sharp contrast to crude bromelain wherein this ratio has been found to be about 3. As the units of protease decrease debriding activity of the mixtures decreases.

The collagenase component of the mixture is measured by the method described in the Worthington Enzyme Manual, Worthington Biochemicals, page 244 (1977). The following materials are used:

Buffer: 0.1 M Tris.$PO_4$ pH 7.4
(0.1 M Tris base titrated to pH with $H_3PO_4$)

Substrate: 6 mg/ml acid-soluble collagen in 0.075 M Na Citrate pH 4 (Calbiochem-Behring Corp. or Sigma)

Optional Addition: 0.05 M $\beta$-mercaptoethanol in buffer

Enzyme Mixture: 0.02 to 0.1 ml of 1 mg/ml (in buffer, saline or water)

Total Volume: 0.5 ml, brought to volume with buffer

Ninhydrin Reagents:

Standard: 5 mM L leucine (Sigma) in $H_2O$ range 0.02 mg to 0.4 mg

Ninhydrin: Dissolve 4 g ninhydrin (Sigma) in 100 ml methyl cellosolve. Add 100 ml 0.2 M citrate buffer, pH 5.0, containing 100 mg $SnCl_2.2H_2O$ Diluent: 1:1 $H_2O$:n-propanol According to the assay, 0.1 ml substrate, 0.1 ml beta-mercaptoethanol, and buffer are mixed together in each test tube (two to four tubes/samples) and warmed to 37° C. The enzyme mixture is added at timed intervals of 30 seconds. The tubes are incubated for 30 minutes at 37° C. in a shaking water bath. The reaction is stopped by removing a 0.2 ml aliquot of reaction mixture and placing it in a test tube with 1 ml ninhydrin solution. The tube is heated for twenty minutes in a boiling water bath. Five ml of diluent is added with vortexing immediately after addition. Absorbance versus a ninhydrin blank is measured at 600 nm on a UV/Visable Spectrophotometer. A leucine standard curve, protein blank, and collagen blank are also run. Results are reported as $\mu$mole leucine/mg enzyme. One unit of activity is equivalent to 1 $\mu$mole leucine released in 30 minutes at pH 7.4 and 37° C.

Active enzyme mixtures of the invention show 0.5 to 5 units of collagenase activity, and preferably 1 to 2 micromoles of leucine per mg of protein activity.

The catechol oxidase component of the mixture is measured by the following method. The materials used are:

Buffer: 0.01 M $NaPO_4$ pH 6.5

Substrate: 10 mM Isoproterenol in $H_2O$, Fresh

Enzyme Mixture: 0.025 to 0.1 ml of 1 mg/ml (in saline or buffer)

Total Volume: 1 ml brought to volume with water.

According to the assay, 0.4 ml buffer, 0.1 ml Isoproterenol and $H_2O$ are mixed together to each tube (2 to 4 tubes are used at each level of enzyme) and warmed to 37° C. At timed intervals of 15 seconds enzyme is added to each test tube. After incubation for 15 minutes at 37° C., the absorbance versus $H_2O$ at 490 nm is read on a spectrophotometer. A sample and substrate blank must be included in the assay.

This assay is terminated by the measurement of color developed after the 15 minute incubation. It is crucial that the test tubes be read exactly 15 minutes after the addition of the sample. One unit is equivalent to an increase in absorbance at 490 nm of 1.000 in 15 minutes at pH 6.5 and 37° C. Active enzyme mixtures of the invention show catechol oxidase activity of 0.1 to 3 units and preferably 0.3 to 0.9 units per mg of protein.

The three enzyme assays described hereinabove require units dependent on the protein content. For purposes of the invention, the assay used for determining protein content is described in *J. Biol. Chem.* 177, 751–766 (1949). The materials used for the assay are as follows:

Biuret Reagent: 1.5 g $CuSo_4.5H_2O$ + 6.0 g $NaKC_4H_4O_6.4H_2O$. Place in 1 liter volumetric flask and add 500 ml $H_2O$ to dissolve. With constant stirring, add (300 ml) 10% NaOH ($CO_3$ free), bring to 1 liter with $H_2O$. Discard if reddish or black precipitate forms.

Standard: 25 mg/ml Bovine Serum Albumin in $H_2O$, Range suggested 0.25 mg–7.5 mg.

According to the assay, 2.5 ml of Biuret Reagent is added to 0.5 ml of sample in solution, with vortexing immediately after addition. The sample is allowed to stand 20–30 minutes at room temperature and the absorbance versus a Biuret Reagent blank at 540 nm. is read on a spectrophotometer. Results are reported in mg protein/mg sample.

A further characterizing parameter of the enzyme mixtures of the invention is their neutral carbohydrate content. This is determined using the anthrone hexose determination method described in R. G. Spiro, Methods in Enzymology 8, pp 1-26 (1966).

According to this method, a 72% solution of $H_2SO_4$ (280 $H_2O$ + 720 ml $H_2SO_4$) is made up, and 500 mg anthrone and 10 g thiourea are dissolved therein while the solution is still warm. Six ml of anthrone solution is added to 1 ml sample of enzyme mixture (dilute to 1 ml with water) and mixed well. The sample is heated in a steam bath for 15 minutes in the dark and cooled in a water bath for ½ hour in dark. The absorbance of the sample is read at 620 nm on a spectrophotometer and compared to a standard using a known quantity of mannose. The enzyme mixture exhibits a neutral carbohydrate content of 0.15 to 0.40 milligram per milligram of protein.

Other methods used to further characterize the enzyme mixtures of the invention include isoelectric focusing and electrophoresis. When the enzyme mixture of the invention was evaluated using isoelectric focusing the following results were obtained:

| Sample Concentration | Acidic Bands pH 3.7 to 5 | Bands at pH 6 to 6.5 | Basic Bands pH 8 to 9.5 |
|---|---|---|---|
| 1 mg/ml | yes | no | yes |
| 5 | yes | no | yes |
| 12.5 | yes | trace | yes |
| 25 | yes | less than 1% | yes |

When compared to crude bromelain (Dole 1200A-VIII-2) by isoelectric focusing at 12.5 mg solid/ml, the enzyme mixture of the invention showed heavy staining in the 7.8-9.3 pH region, whereas the crude bromelain was barely visible in this region. This indicates an enrichment in the collagenase-protease component of the enzyme mixture over the crude bromelain on a weight basis.

When the enzyme mixture was evaluated using disc polyacrylamide gel electrophoresis (carried out as described by Brewer and Ashworth, J. Chem. Ed. 46:41 (1969), nine bands were found at pH 8.3 and five bands were found at pH 4.3 applying 125 μg and 250 μg samples respectively.

The enzyme mixture of the invention gives three major peaks when molecular weight evaluation is carried out on Sephadex G-100. A 2.5×80 cm column is equilibrated with 0.05 $MH_3BO_4$ and titrated to pH 7.4 with NaOH. Seven hundred fifty mg of enzyme mixture, at 100 mg/ml in column buffer, is applied. Peaks are found at 45,000, 32,000, and 25,000 daltons. The fraction peaking at 45,000 daltons has catechol oxidase activity. The fraction peaking at 25,000 daltons has protease activity.

The process for preparing the enzyme mixture used in the method of the invention involves suspending commercially available stem bromelain in a solution of a weakly basic buffer having a pH of about 8 to 10.5 to selectively solubilize the active components. Undissolved solid is then removed from the suspension by conventional techniques. The solution obtained is further purified to remove small molecules having a molecular weight of about 10,000 or less to form a solution of the active component in water. Further steps include removal of the water-insoluble products formed in the preceding purification step, concentration of the solution by reducing the water content, lyophilization for stability during storage and sterilization prior to applying the enzyme mixture to devitalized tissue.

The crude bromelain useful as a starting material for the process may be obtained as "Dole Bromelain 1200", from Castle and Cooke Foods, P. O. Box 3380, Honolulu, Hawaii; and "Bromelain" from Tai Li Enzymes Industrial Co., Ltd., Taiwan.

Commercially available bromelain is known to be prepared from the stem of the pineapple plant. The juice from the stem is first adjusted to a pH of about 3 or 4 with phosphoric acid, and sodium sulfhydride is added to protect against sulfhydryl oxidation. The inert material is precipitated in about 30% acetone (addition of sufficient acetone so that the solution is 30% in acetone) or other suitable solvent and, after filtration, the clarified fluid is precipitated with 70% acetone. This precipitate is collected by centrifugation and either dissolved in water containing sodium sulfhydride which has been acidified with phosphoric acid and reprecipitated, or dried in a vacuum oven directly. If the material is reprecipitated, 70% acetone is utilized. The dried material from either process is suitable as a starting material for the process of the present invention.

In the first step of the process, the crude bromelain is suspended in a weakly basic buffer solution. Aqueous buffers are preferred to minimize denaturization of the active enzymes, although other solvents which do not adversely affect the activity of the enzymes could be used. Of the weakly basic buffers sodium borate is preferred, but other buffers which are acceptable include those with a pKa of about 8 to 10.5 such as disodium phosphate, trishydroxymethylaminomethane hydrochloride, sodium glycylglycine, sodium glycinate, glycinamide hydrochloride, cyclohexylaminoethanesulfonic acid and cyclohexylaminopropanesulfonic acid.

Borate buffers are especially preferred because they temporarily inhibit enzymatic activity of the mixture, producing less reaction with naturally present enzymes and other substrates. This results in less darkening and tarring of the mixture and avoids the usual loss of some enzymatic activity.

The strength of the buffering solution is generally 0.01 to 1.0 M and is preferably 0.01 to 0.2 M. The concentration of the preferred buffer, sodium borate, is limited by low solubility at room temperature and below. The temperature of the solution is generally maintained below 20° C., and preferably below 10° C., to minimize denaturization of the active enzymes. The ratio of buffer solution volume (milliliters) to weight of crude bromelain (grams) is generally from 5 to 1 to 40 to 1, and preferably from 8 to 1 to 12 to 1.

The buffering solution dissolves substantially all of the desired active enzymes. Generally, the solution is stirred for a period of 2 to 4 hours for maximum solubilization. The undissolved material is then removed by conventional methods such as filtration or centrifugation. The primary criterion for the separation method is that the resulting solution be suitable for the next step, which involves the removal of small molecules having a molecular weight of about 10,000 or less. The presently preferred method of separation is by pressure filtration using a filter aid, e.g., cellulose filter aid, to minimize problems associated with the sticky, gelatinous residue clogging the filtering apparatus.

The removal of the small molecules from the resulting solution can be accomplished using conventional techniques such as dialysis or diafiltration. Diafiltration is preferred for large scale production.

When the filtrate is dialyzed, water is generally used on one side of the dialysis membrane with the filtrate on the other in a volume to volume ratio of 1 to 10 filtrate to water. Dialysis is continued until a substantial portion of the small molecules have been removed; usually about five dilutions is sufficient. Measurement of the sugar content of the dialysate is a convenient indicator of the end point of dialysis. By the anthrone method of sugar measurement, the end point is about 800 μg/ml.

Although not necessary to enhance the debriding activity of the product, it may be desired for purposes of characterization of the product to subject the solution obtained from dialysis to a cationic exchange process. If this is contemplated, a weakly basic buffer such as boric acid may be used instead of water as the dialyzing fluid. The concentration of the dialyzing fluid in that case is generally 0.01 to 1.0 M, and is preferably 0.02 to 0.75 M. The pH of the solution is generally 7.5 to 9.5 and is preferably 8.0 to 9.0. The purpose of dialysis versus a weakly basic buffer is to remove small molecules from the solution and to obtain a sample which is suitable for ion exchange. In a typical ion exchange process, a cationic exchange resin, e.g., Sephadex CM-50 (a hydrophilic dextran polymer with carboxymethyl groups attached giving the polymer a negative charge, obtained from Pharmacia, Piscataway, N.J.) is used, eluting first with 0.05 M boric acid, pH 8.5, then with a stronger ionic strength buffer, e.g., making the borate buffer 0.25 M in sodium chloride solution. The resin may be used in either batch or column style. The eluate obtained is dialyzed against water to remove borate and sodium chloride.

During dialysis, buffering material diffuses out and some finely-divided water-insoluble precipitates form which are desirably removed from solution by conventional methods such as filtration or centrifugation prior to preparing the solution for use or storage. The solution is preferably lyophilized to stabilize the active ingredients until the time of use. At some point prior to use, either before or after lyophilization the product must be sterilized to avoid contaminating the wound with microorganisms. Conventional sterilization techniques which do not measurably affect the activity of the enzymes such as passage through a Millipore® filter may be used.

When preparing large batches of product, it is preferred to remove the small molecules from the buffer solution by diafiltration instead of dialysis. The preferred method of diafiltration involves forcing the filtrate under pressure through a cartridge containing hollow fibers. As the filtrate flows along the thin channel inside each fiber, small molecules pass out of the fiber. To compensate for the water which is lost through the fibers, water is added during the process to maintain the retentate volume at the original volume of the starting solution. Diafiltration apparatus of this type is available from Amicon Corporation (Scientific Systems Division, Lexington, Mass.) and Romicon, Inc. (100 Cummings Park, Woburn, Mass.). Hollow fiber cartridges designed to remove small molecules having a molecular weight of about 10,000 or less are used.

Diafiltration is continued until a substantial portion of the small molecules is removed. It has been found that on the equipment used, this diafiltration step is sufficiently complete when the diafiltrate volume is about three times the retentate volume. However, this ratio may vary with the characteristics of the equipment used. An accurate determination of when to cease diafiltration can be made by analysis of the rententate. Values similar to those given in Example 1 below indicate diafiltration can be stopped.

Like dialysis, diafiltration produces some finely divided water-insoluble precipitates which may gradually clog the hollow fiber pores. Intermittent separation of these precipitates may be necessary. This is preferably done by shunting the retentate through an auxillary centrifugation or filtration apparatus during the diafiltration process so that complete interruption of diafiltration is not necessary.

After diafiltration is completed, it is desirable to concentrate the solution prior to lyophilization. This is preferably accomplished by passing the solution through the hollow fiber apparatus again, but this time without replacing water. This mode of operating the apparatus to concentrate the solution is termed ultrafiltration.

The concentrated solution obtained through ultrafiltration is preferably lyophilized to maintain stability. A solid product in a yield of about 20 to 40% is provided. Alternatively, the concentrated solution is filtered under sterile conditions to provide a sterile solution which is packaged in a vial which may be lyophilized to provide a sterile powder.

The enzyme mixture is prepared for application to the devitalized tissue by dissolving or suspending the lyophilized powder in a suitable vehicle. Alternatively, concentrated solutions of the enzyme mixture can be further diluted with a vehicle, e.g., a viscous or semi-liquid vehicle.

A preferred composition for the administration of the enzyme mixture of the invention is a sterile aqueous solution. Such solutions are readily prepared by dissolving up to 20% by weight of the lyophilized enzyme powder in water. Aqueous solutions are not stable for extended periods. More concentrated solutions deteriorate more rapidly.

Other methods useful for administration of the enzyme mixtures of the invention include incorporating into aqueous solutions various gelling agents such as polyols e.g., Carbopols, (available from Goodrich Chemical Co.) carboxyvinyl polymers e.g. Pluronics (available from BASF Corporation), Veegum HV (R. T. Vanderbilt Company, Norwalk, Conn.) and the like. These are buffered using various agents which provide a buffered pH of about 7.4, e.g., disodium phosphate ($Na_2HPO_4$) and imidazole. The buffering agents are generally used in concentrations of 0.05 to 0.2 M. The gelling agents are generally used in concentrations of 1 to 2% for polyols and about 18% for carboxyvinyl polymers and about 6% for Veegum HV. Pluronic F-124 and Carbopols 940 and 934 and Veegum HV are presently preferred gelling agents.

The formulations are prepared by mixing the vehicle, then adding the lyophilized enzyme mixture shortly (e.g., 1 hour) before use.

The formulations of the enzyme mixtures of the invention may also be used with other active ingredients. For example, antibiotics or other chemotherapeutic agents useful to prevent infection may be added to the formulations.

For various purposes, the enzyme mixtures of the present invention are provided as solids e.g., lyophilized powders or as suspensions or solutions. When aqueous solutions are provided it is preferred to prepare them immediately before use, since aqueous solutions have been found to slowly and gradually decompose.

The efficacy of the enzyme mixtures of the invention was evaluated against burn eschar in pigs. Third degree burns were obtained by radiant heat or scald-type burns. The eschar was treated either before or after hardening by application of a solution or other formulation of the enzyme mixture.

Removal of the eschar may be attempted and carried out periodically, or one can wait for a more extended time and remove it all at once. If removal is periodic, more of the enzyme mixture is generally applied. Occlusion of the eschar is helpful to maintain moisture and warmth in the treatment area. Warming skin to 35° to 37° C. using a hot water blanket accelerates debridement.

If the eschar is allowed to harden before treatment, presoftening with a moisturizer, e.g., normal 0.9% saline solution may be desirable. Thick intact epidermis was removed prior to the treatment on pigs. In general, eschar treated with the enzyme mixture according to the invention can be easily wiped off or lifted off without any difficulty.

Further description of the invention is provided by the following non-limiting examples:

EXAMPLE 1

To a clean 10 gallon glass lined Pfaudler reactor was added 38 l of ultrapure water containing 1087 g of sodium borate; 10 hydrate ($Na_2B_4O_7.10H_2O$). Ultrapure water was obtained by treatment of building supplied distilled water with a Millipore ® "Super Q Ultrapure Water System." The water was pumped in series through a carbon filter, ion exchange filter, and a 0.22 $\mu M$ filter. Purity was measured by resistance and equaled 18 megohm-cm or better. The solution was cooled to 5° C. and 3.80 kg of crude Dole bromelain was added in portions over 10 minutes. The reactor stirrer was maintained at 120 rev/min during the addition and for 15 minutes thereafter. The stirring rate was decreased to 80 rev/min and the reactor was purged with nitrogen. The slurry was stirred for 195 minutes. Cellulose filter aid, prewashed in ultrapure water (570 g) was added to the reactor and the mixture slurried for several minutes. The mixture was pressured, using nitrogen (5–10 psi), through a jacketed stainless steel "Sparkler" filter containing cellulose filter pads previously treated with 570 g of washed cellulose filter aid. Cold water was circulated through the filter jacket to maintain the internal temperature at 5° C. The filtration slowed quickly requiring 45 minutes for completion. The filter was rinsed with 3.8 l of 0.075 M $Na_2B_4O_7.10$ $H_2O$ and the combined filtrate was stored in a stainless steel container in a cold room (5° C.) overnight. Examination of the "Sparkler" filter revealed it contained approximately 1 gallon of solution which had not been filtered. Because the solution had warmed to room temperature overnight it was discarded.

The cold aqueous filtrate was transferred to the storage tank of a clean "Romicon" Model HF2SSS ultrafiltration apparatus equipped with two "Romicon" Model HF-15-43-PM-10 hollow fiber cartridges having a molecular weight cutoff of 10,000 and an effective surface area of 15 ft². Each individual hollow fiber has an inside diameter of 43 mil. The "Romicon" apparatus had previously been modified to include two stainless steel heat exchangers one inserted in front of, and one behind, the cartridge. Diafiltration was started by pumping the solution through the hollow fiber cartridge at 15 psi. The back pressure, or pressure of the solution as it exists in the end of the hollow fibers, was adjusted to 10 psi. The initial temperature of the solution increased to 10° C. but cooling water circulating in the heat exchangers quickly decreased the temperature to 4° C. The diafiltrate solution forced through the hollow fiber walls was collected in a separate tank. The volume of the circulating solution (or retentate) was maintained at 10 gallons through periodic addition of chilled ultrapure water. Samples of the diafiltrate beginning at 2.5 gallons and at 5 gallon intervals through the process were taken for analysis. As expected from previous small scale work, a fine solid began to precipitate from solution decreasing the rate of diafiltration through the hollow fiber walls. After 6.5 hours 20 gallons of diafiltrate had been collected, but a very slow diafiltration rate forced a stoppage. The bromelain solution (retentate) was drained from the apparatus amd stored overnight in a cold room (5° C.). The apparatus was rinsed with tap water, drained, filled with 5 gallons of a solution containing 1 lb of $Na_2B_4O_7.10$ $H_2O$, and allowed to stand overnight.

The enzyme solution mixed with 1 lb of washed cellulose filter aid was transferred to a clean 10 gallon glass reactor and, through cooling, maintained at 5° C. The solution was pressured with nitrogen (5–10 psi) through a 10 micron filter into a chilled stainless steel container over a 2 hour period. This solution was stored in a cold room (5° C.) overnight. The "Romicon" ultrafiltration apparatus was prepared by backflushing at 10 psi approximately 2.5 gallons of diafiltrate back through the hollow fibers then draining the apparatus. The apparatus was flushed with ultrapure water, drained, and chilled. The filtered enzyme solution was re-added and the diafiltration was continued with the temperature again maintained at 5° C. and the retentate volume maintained at 10 gallons. As diafiltration continued a fine precipitate again formed, slowing the diafiltration rate. The total volume of filtrate increased from 20 to 25 gallons after 3 hours, to 27.5 gallons after 5.5 hours, and to 30 gallons after 7 hours. Previous work on small scale hollow fiber equipment had indicated that the diafiltration was complete after the diafiltrate volume was three times the retentate volume. The enzyme (retentate) solution was drained and stored in a stainless steel container in a cold room (5° C.).

The samples of the diafiltrate were tested by: (1) absorbance versus water at 260 nm and 280 nm and found to have an optical density of at least 0.99 and 1.15, respectively; and (2) ninhydrin protein determination (Worthington: Enzymes (1972) pp. 138–139; 2 mm leucine as standard). The value obtained was at least 2.4 mM. Comparison against a reference solution and previously run small scale runs indicated completion by both the absorbance and ninhydrin protein tests. A sample of the enzyme solution was analyzed for protein, carbohydrate, protease, collagenase, and catechol oxidase. The values obtained are reported below.

The enzyme solution was transferred to a chilled 10 gallon reactor together with approximately 1 lb of washed cellulose filter aid and pressured with nitrogen (5–10 psi) through a 3 micron cotton string filter over a 90 minute period. The filter was rinsed with 1 gallon of ultrapure water and the combined filtrate was stored in a stainless steel container in a cold room (5° C.). A 0.25% sodium azide solution which had been added to the hollow fiber cartridges to prevent spoilage was drained and the apparatus was flushed three times with 10 gallons of water. After the hollow fibers were backflushed with ultrafiltrate, the apparatus was flushed twice with 10 gallons of ultrapure water and drained. The enzyme solution was added and ultrafiltration started. The solution (retentate) was again kept cold, however, the solution volume was not maintained constant as in the diafiltration step, but allowed to concentrate. After 2.5 hours of operation the retentate solution, still clear, had been concentrated to 7.5 gallons and was drained and stored in a cold room for 4 days.

The concentrated enzyme solution was lyophilized on a 10 port center well freeze drier in three runs. To a 5 liter single neck glass round bottom flask was added 1.3 liters of the enzyme solution. The flask was turned in a dry ice bath for 20 minutes to shell freeze the solution on the flask walls. The flask was then placed on the freeze drier under vacuum (0.05 mm Hg). The lyophilization of 13 liters (10 flasks) under vacuum of 0.05–0.4 mm Hg required 63 hours. The resulting light solid was collected except for one flask which had a small amount of wet solid (melt down). This wet solid was removed and discarded and the remaining dry solid from this flask was redissolved in the remaining enzyme solution. The remaining enzyme solution was lyophilized in two runs of 10 liters (1 liter per flask) and 2 liters (0.5 liter per flask) each. The material experienced no melt down and required 46 hours and 23 hours, respectively, for completion. The total collected solid from the three runs yielded 1,099 g (28.9%) of a light tan low density solid. The product obtained after diafiltration and prior to lyophilization was carefully analyzed. It had the following properties:

| | | |
|---|---|---|
| Protein Content (Biuret method as Bovine Serum Albumin) | | 23 mg/ml |
| Neutral Carbohydrate Content (Anthrone method as mannose) | | 0.45 mg/mg protein |
| Protease (azoalbumin substrate | with R—SH | 27 units/mg protein |
| | no R—SH | 2.7 units/mg protein |
| Collagenase | with R—SH | 7.5 mole leucine/mg protein |
| | no R—SH | 4.5 mole leucine/mg protein |
| Catechol Oxidase (isoproterenol substrate) | | 2.1 units/mg protein |

EXAMPLE 2

The method of the present invention was evaluated against devitalized tissue in pigs producing by scalding burns according to the method of Winter (Trans. 3rd Int. Congress on Research in Burns, Prague, Sept. 20–25, 1970, p. 614).

The upper thoracic area of each of two anesthetized Yorkshire-Duroc pigs (20 to 40 kg) was shaved and scalded on four 16 cm² circular sections by treating with circulating hot (80° C.) water for 30 seconds. A hollow cylinder was held tightly against the skin and 40 ml of hot water added. The cylinder was equipped with means for recirculating the water to keet it at constant temperature ($\pm 1°$ C.) throughout the 30-second period. The epidermis was removed from the burned area as soon as it cooled. After 48 hours the eschar of the third degree burns had hardened. The eschar was soaked for one hour with gauze saturated with 0.9% sodium chloride solution. Test samples of the enzyme mixture prepared as described in example 1 (2 ml of a 10 mg/ml saline solution in a gauze pad) were applied to four of the sites and a saline controls applied to the other four sites. The sites were occluded with saran wrap for two hours. After two hours the sites were wiped off and a second application of the same sample was applied as before. After another 2 hour (4 hour total) the sites were evaluated. By visual and histological examination, it was observed that all of the eschar was removed from the treated sites by rubbing with a tongue depressor. The eschar was not removable from the control sites.

EXAMPLE 3

Two Yorkshire-Duroc piglets, 6 to 8 weeks old, were scaled on four 16 cm² sections of the upper thorax by treating with hot (80° C.) water for 30 seconds as described in Example 2. After 48 hours the eschar of the third degree burns had begun to harden. The eschar was soaked for one hour with 0.9% sodium chloride solution. Test samples were applied and occluded for two hours. The eschar was wiped off and another test sample was applied for a second two-hour period.

When a two ml dose of enzyme mixture (5 mg/ml in saline) was applied to two of the sites and saline was applied as a control to the other two sites, all of the eschar was removed from the treated sites, while the eschar was not removable from the control sites.

EXAMPLE 4

Four to six week old Yorkshire-Duroc piglets were exposed to radiant heat of 360° C. for twenty seconds on four 10 cm² sites using the method of Klein. (South African Pat. No. 77/0209).

One hour after burning the eschar was treated with 2 ml of the test enzyme mixture (10 mg/ml in saline) on two of the sites, and saline was applied as a control to the other two sites on each pig. By visual and historical observation all of the eschar was removed from the treated sites after 4 hours of treatment. This eschar was not removable from the control sites.

EXAMPLE 5

The following formulations of the enzyme mixture of the invention were prepared by adding 10 mg per g of the lyophilized powder enzyme mixture to an aqueous solution of the buffered gelling agent. Two grams of each formulation were successfully used to treat burn eschar in pigs.

TABLE I

| Formulation* | Gelling Agent | Buffer | % Propylene Glycol |
|---|---|---|---|
| A | 1.5% Carbopol 940 | 0.1M Na₂HPO₄ | 10 |
| B | 18% w/v Pluronic F-127 | 0.1M Na₂HPO₄ | 0 |
| C | 2% Carbopol 934 | 0.1M Na₂HPO₄ | 10 |
| D | 1% Carbopol 934 | 0.1M Imidazole | 10 |
| E | 1% Carbopol 934 | 0.1M Imidazole | 10 |
| F | 1% Carbopol 934 | 0.1M Imidazole with 0.1M NaCl added | 10 |
| G | 1.5% Carbopol 940 | 0.05M Na₂HPO₄ | 10 |
| H | 1.5% Carbopol 940 | 0.1M Na₂HPO₄ | 10 |
| I | 1.5% Carbopol 940 | 0.2M Na₂HPO₄ | 10 |
| J | 6% Veegum HV | 0.1M Na₂HPO₄ | 30 |
| K | 1.5% carbopol 940 | 0.1M Na₂HPO₄ | 0 |

*All formulations contained about 0.2% methyl parabens as the preservative system.

What is claimed is:

1. A method of treating devitalized mammalian skin tissue comprising the steps of:
   a. applying to said tissue an effective amount of a composition comprising an enzyme mixture derived from crude bromelain by
      i. suspending the crude bromelain in a solution of a weakly basic buffer having a pH of about 8 to 10.5 to selectively solubilize the active components;
      ii. separating the undissolved solids from the solution; and
      iii. removing a substantial portion of the small molecules having a molecular weight of about 10,000 or less from said solution;
   in an inert solvent carrier containing at least sixty percent water;
   b. allowing said composition to loosen said devitalized tissue and;
   c. removing said devitalized tissue.

2. A method of treating devitalized mammalian skin tissue comprising the steps of:
   a. applying to said tissue an effective amount of a composition comprising an enzyme mixture derived from crude bromelain by:
      i. suspending the crude bromelain in a solution of a weakly basic buffer having a pH of about 8 to 10.5 to selectively solubilize the active components;
      ii. separating the undissolved solids from the solution;
      iii. removing a substantial portion of the small molecules having a molecular weight of about 10,000 or less from said solution;
      iv. removing any precipitate formed in step iii from the resulting solution;
      v. concentrating said resulting solution; and
      vi. lyophilizing said resulting solution;
   in an inert solvent carrier containing at least sixty percent water;
   b. allowing said composition to loosen said devitalized tissue; and
   c. removing said devitalized tissue.

* * * * *